US00PP30339P2

(12) United States Plant Patent
Hansen

(10) Patent No.: US PP30,339 P2
(45) Date of Patent: Apr. 2, 2019

(54) ***COLOCASIA* PLANT NAMED 'BLACK GOBLET'**

(50) Latin Name: ***Colocasia* hybrid**
Varietal Denomination: Black Goblet

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,772

(22) Filed: Apr. 23, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373, 263.1, 258
CPC ..... A01H 5/12; A01H 5/02; A01H 5/00
See application file for complete search history.

*Primary Examiner* — Kent L Bell

(57) ABSTRACT

A new and distinct cultivar of *Colocasia* plant named 'Black Goblet' characterized by large lustrous dark greyed-purple leaf blades that are deeply cupped. The leaf blades are held nearly horizontally. The tropical stemless perennial produces multiple, long, spadix flowers with burgundy spathes.

2 Drawing Sheets

Botanical classification: *Colocasia* hybrid.
Cultivar designation: 'Black Goblet'.

CROSS REFERENCE TO RELATED APPLICATIONS

This application is co-pending with the U.S. Plant Patent Applications for two other plants from the same breeding program with the same parents, namely, *Colocasia* plant named 'Black Swan' co-pending U.S. Plant patent application Ser. No. 15/932,163 and *Colocasia* plant named 'Distant Memory' co-pending U.S. Plant patent application Ser. No. 15/932,164.

BACKGROUND OF THE PLANT

The present invention relates to a new and distinct hybrid of *Colocasia*, hereinafter referred to by its cultivar name, 'Black Goblet'. *Colocasia* is a tropical genus in the Araceae family.

The new cultivar was derived from a controlled breeding program performed by the inventor at a wholesale perennial nursery in Zeeland, Mich., USA. The overall purpose of the breeding program is to make selections of *Colocasia* plants with colorful foliage, good growth rate that are well suited for landscape or containers. 'Black Goblet' arose from a cross performed in May 17, 2012 between *Colocasia* 'Black Coral' U.S. Plant Pat. No. 23,896 as the female and the male parent was 'Thailand Giant' (not patented). 'Black Goblet' was given the breeder code 12-07-03 prior to naming.

Asexual propagation of the new cultivar was first accomplished by in vitro propagation using shoot tip culture in 2014. To those skilled in the art shoot tip tissue culture produces propagules of identical characteristics to those of the original plant. Asexual propagation of 'Black Goblet' by shoot tip tissue culture has shown that the characteristics of the new cultivar are stable and reproduce true to type in successive generations.

SUMMARY OF THE INVENTION

Plants of *Colocasia* 'Black Goblet' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of the new plant and distinguish it as a new and distinct *Colocasia* different from all other *Colocasia* known to the inventor:

1. Large, cupped, lustrous, dark greyed-purple leaves;
2. Large, upright, stemless, vigorous, tropical perennial habit;
3. Multiple, long, spadix per leaf axil.

BRIEF DESCRIPTION OF THE DRAWINGS

The photographs of the new plant demonstrates the unique traits and the overall appearance of *Colocasia* 'Black Goblet'. The colors are as accurate as reasonably possible with color reproductions of this type. Variations in ambient light spectrum, source and direction may cause the appearance of minor variation in color. The plants used in the photograph were two-year-old plants grown initially in a greenhouse then set out in mid-spring in a shaded trial garden at a wholesale perennial nursery in Zeeland, Mich. with supplemental water and fertilizer when needed. No plant growth regulators or pinching have been used.

Figure 1:
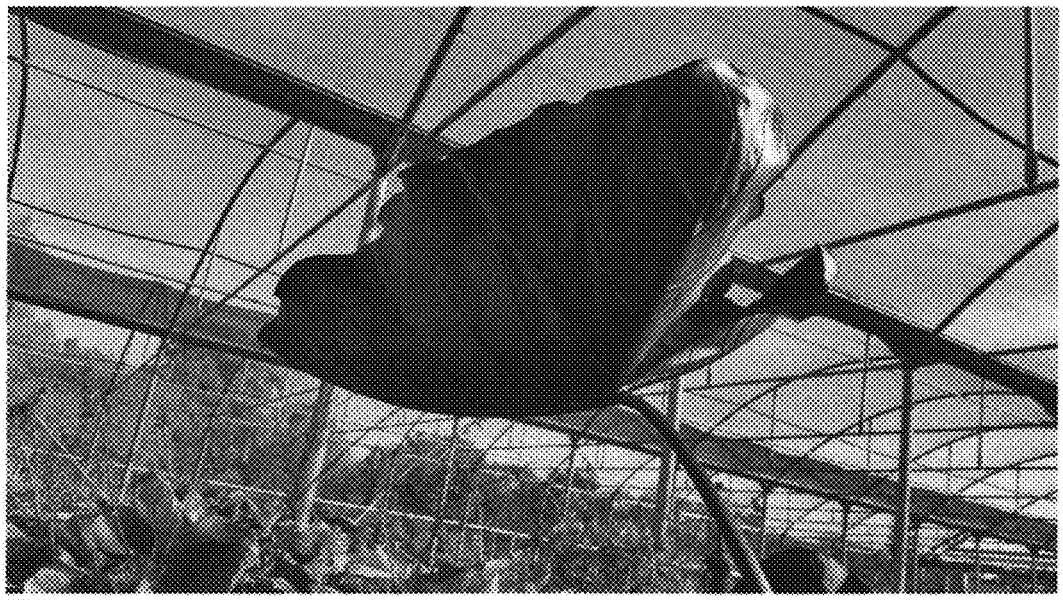
FIG. 1 shows the lower view of the leaf.
Figure 2:
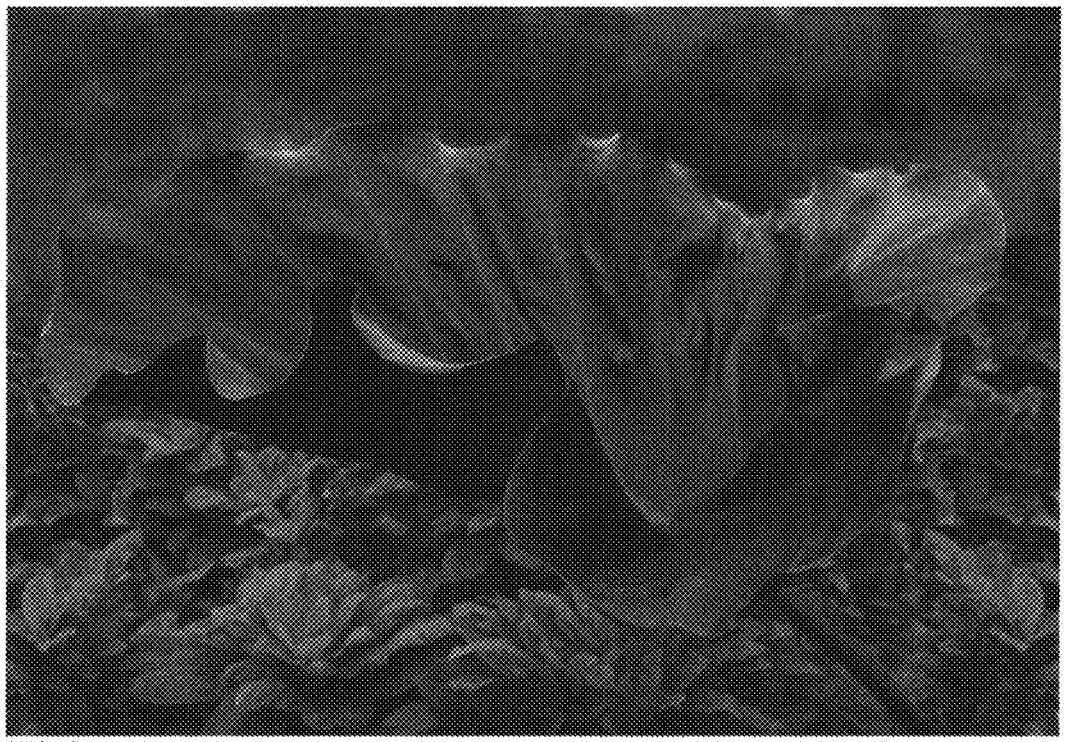
FIG. 2 shows the upper view of the leaf
Figure 3:
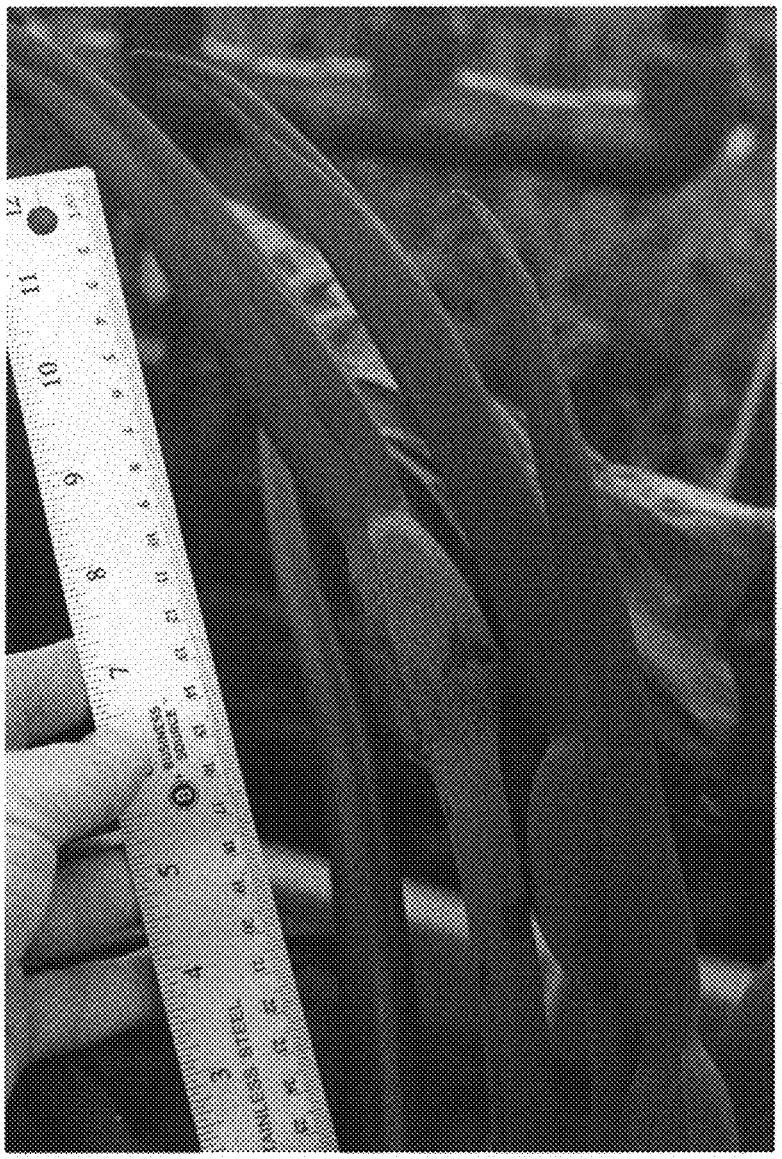
FIG. 3 shows the flowers with ruler for size reference.

The nearest comparison varieties known to the inventor are the co-pending siblings 'Black Swan' and 'Distant Memory', 'Black Sapphire Gecko' U.S. Plant Pat. No. 27,966 and 'Coffee Cups' (not patented).

In comparison to the new plant, the female parent, 'Black Coral', is smaller in habit and individual leaf blades and the leaf blades are more drooping with less cupping. The male parent, 'Thailand Giant' is larger in habit with larger leaves, and the leaf blades and petioles are medium green colored and the adaxial leaf surface is dull rather than the greyed-purple leaf blade and petiole and lustrous adaxial leaf surface of the new plant.

'Black Goblet' has larger leaf blades than 'Black Sapphire Gecko' and leaves of the new plant are held more outright, more cupped and less cernuous than 'Black Sapphire Gecko'. Compared with 'Distant Memory' the new plant has more lustrous upper leaf surfaces and is larger in habit with fewer side shoots and the leaf blades are more cupped. Compared with 'Black Swan' the new plant has less flat and more cupped leaf blades, and the leaves are smaller and lighter greyed-purple. 'Coffee Cups' is slightly larger in plant habit, with smaller leaf blades of olive-green that are held more upright, but the leaf blades are similarly cupped.

DETAILED BOTANICAL DESCRIPTION

The following is a detailed description of two-year-old plants of the new cultivar as grown initially in a greenhouse and then outdoors, in a shaded trial garden in Zeeland, Mich. No plant growth regulators have been used. Plants of the new cultivar have not been tested under all possible conditions. The phenotype may vary with changes in environmental, climatic, and cultural conditions without change however in the genotype. The color reference is in accordance with the 2015 edition of The Royal Horticultural Society Colour Chart except where general color dictionary terms are used.

Botanical designation: *Colocasia* hybrid;

Cultivar denomination: 'Black Goblet';

Parentage: The female or seed parent is 'Black Coral' and the male or pollen parent is 'Thailand Giant';

Asexual propagation: Shoot tip tissue culture;

Time to initiate roots: About two weeks;

Time to finish in a 7 liter container: About three months from a 2.5 cm plug;

Growth rate: Vigorous;

Plant habit: Tropical herbaceous perennial; upright; acaulescent; upright; clumping;

Plant size: About 102.0 cm tall and about 160 cm wide at edges of leaves;

Root description: Thick, limited branching; to about 25.0 cm long;

Root color: Between RHS 182A and RHS 183D;

Foliage: Sagittate to cordate; simple; calathiform; slightly and irregularly sinuate; slightly dimpled; base auriculate, frequently imbricate to partially fused; apex broadly acute; margin entire; both adaxial and abaxial surfaces lustrous and glabrous;

Leaf size: About 40.0 cm long from apex to tip of auricule, about 30.0 cm long from petiole to apex, auricula about 10.0 cm long from petiole to auricule tip, about 30.0 cm across toward middle of leaf, about 15.0 cm deep sinus from petiole to line across leaf margins;

Leaf color: Young adaxial nearest RHS 146B, young abaxial nearest RHS N186C; mature adaxial nearest RHS N186A, mature abaxial nearest RHS 187A;

Veins: Pinnate; glabrous abaxial and adaxial; main veins broad, nearly smooth adaxial and costate and rounded abaxial;

Vein size: Abaxial midrib about 9.0 mm across at petiole with two main lateral veins in auricula about 8.0 mm across and other secondary veins about 3.5 mm across; adaxial midrib about 6.0 mm across with two lateral veins in auricula about 5.0 mm across with secondary veins about 2.5 mm across;

Vein color: Young adaxial between RHS N186C and RHS N186D, young abaxial nearest RHS 187C; mature adaxial between RHS N187A and RHS N186A, mature abaxial veins between N186C and RHS 187B;

Leaf blade attitude: Nearly horizontal;

Petioles: Sarcous; strongly concavo-convex to involute; attitude upright to semi-outwardly;

Petiole size: Average about 80.0 cm long, 20.0 mm across and 22.0 mm deep at base and 6.0 mm across below leaf blade;

Petiole color: Abaxial nearest N186A, adaxial nearest RHS 189A;

Inflorescence description: Spadix surrounded by a spathe, female portion proximal to male portion on same peduncle; beginning to bloom about mid-August in Michigan once plants mature; typically two per node;

Inflorescence size: Average about 22.0 cm in length and 2.6 cm in width;

Inflorescence bud: Linear to slightly clavate with swollen rounded base; apex narrowly acute; about 14.0 cm long and 2.2 cm diameter;

Inflorescence bud color: Variable depending on portion; nearest RHS N186D in distal portion and nearest RHS N186B in swollen base;

Flower fragrance: None detected;

Lastingness of inflorescence: About 2 to 3 weeks;

Flower quantity: Average about 200 female flowers sessile to spadix; average about 500 sessile male flowers per spadix;

Spathe: Hooded involute bract; subtending spadix and completely enveloping spadix; coriaceous; lanceolate with acute apex and truncate base; margin entire;

Spathe size: Average about 22.0 cm total length, 6.5 cm long at gynoecium, 15.5 cm long at distal to androecium, 2.8 cm diameter at gynoecium and 2.0 cm diameter at androecium, 1.2 cm diameter at constriction between androecium and gynoecium; manually spread open to about 9.5 cm wide;

Spathe color: Abaxial nearest RHS N186D in distal portion and nearest RHS N186B in swollen base; adaxial portion nearest RHS 186D;

Spadix: Male portion with narrowly acute apex, average about 9.0 cm long and 1.3 cm diameter; female portion proximal male portion, female portion ellipsoidal, about 2.5 cm long and 2.5 cm diameter in widest portion;

Spadix color: Nearest RHS 161D;

Peduncle: Terete, slightly flattened on one side; glaucous; glabrous; mostly upright; about 58 cm long and 12.0 mm diameter at base; emerging from leaf axils;

Peduncle color: Nearest RHS N187B;

Reproductive organs: Have not been observed to develop;

Fruit and seed: Have not been observed;

Diseases and resistance: Resistance to pests and diseases beyond that common for other *Colocasia* cultivars has not been observed. The plant is tropical and grows best with ample moisture, good drainage and warm temperatures. The complete hardiness of the new plant has not been tested.

It is claimed:

1. A new and distinct cultivar of *Colocasia* plant named 'Black Goblet' as herein illustrated and described.

* * * * *